United States Patent [19]
Doddington et al.

[11] 4,020,677
[45] May 3, 1977

[54] APPARATUS FOR DETERMINING SALINITY OF FLUIDS

[75] Inventors: Harold W. Doddington; Donald M. Sheppard, both of Gainesville, Fla.

[73] Assignee: The United States of America as represented by the Secretary of the Navy, Washington, D.C.

[22] Filed: June 17, 1976

[21] Appl. No.: 697,304

[52] U.S. Cl. .............................. 73/61 R; 73/170 A; 324/30 B
[51] Int. Cl.² ....................................... G01N 27/08
[58] Field of Search ...................... 73/61 R, 170 A; 324/30 B

[56] References Cited
UNITED STATES PATENTS

| | | | |
|---|---|---|---|
| 2,939,070 | 5/1960 | Rosenthal | 324/30 B |
| 3,181,058 | 4/1965 | Gulbrandsen | 324/30 B |
| 3,263,224 | 7/1966 | Berman et al. | 324/30 B X |
| 3,748,899 | 7/1973 | Gregg et al. | 73/170 A |
| 3,774,104 | 11/1973 | Andersen | 324/30 B |
| 3,963,979 | 6/1976 | Dauphinee | 324/30 B |

*Primary Examiner*—Richard C. Queisser
*Assistant Examiner*—Joseph W. Roskos
*Attorney, Agent, or Firm*—R. S. Sciascia; Paul S. Collignon

[57] ABSTRACT

An instrument for determining salt concentration in water by measuring electrical conductivity. A probe of electrical insulating material has one electrode mounted on the exterior surface of the probe and a second electrode is mounted in a cavity in the probe. A horizontal slit is provided at one end of the probe and a small vertical hole connects the horizontal slit with the cavity to provide a fluid passageway. A sinusoidal current excitation source is provided to energize the probe and the electrical current density between the two electrodes is small except in the vertical hole where the current density becomes very large. The resistance between the electrodes at any instant is governed by the resistance of the fluid in the vertical hole. The resistance of the fluid is measured by processing the voltage which exists between the two electrodes of the probe through a differential amplifier, rectifier, filter and output amplifier arrangement to provide a voltage output which is inversely proportional to the salinity of the fluid being tested.

5 Claims, 4 Drawing Figures

APPARATUS FOR DETERMINING SALINITY OF FLUIDS

BACKGROUND OF THE INVENTION

The present invention relates to a measuring device for determining salt concentration in water and more particularly to a device for measuring the variation of mass density along a vertical line.

One accurate and convenient way of measuring salt concentration in water is to measure the electrical conductivity of the solution. Various types of instruments are available for measuring conductivity of fluids. For example, in U.S. Pat. No. 3,748,899, entitled "Conductivity And Temperature Sensing Probe", which issued July 31, 1973, to Michael C. Gregg and Charles S. Cox, there is shown and described a probe for measuring the vertical profile of temperature and salinity in the ocean. In this patented device, sensing means are provided consisting of a pair of inner and outer electrodes which are employed to determine voltage variations across a small chamber opening, these variations being due to fluctuations in electrical resistance which in turn is related to the temperature and salinity of the ocean medium. To provide the voltage for this sensing means, a separate driving means, such as a pair of electrodes, are used to apply a constant amplitude electrical current across the opening, the sensing means measuring the variations in this constant amplitude.

While instruments developed for ocean measurements, such as the one described in U.S. Pat. No. 3,748,899, can measure the vertical profile of temperature and salinity, these heretofore available devices do not provide sufficient resolution required by a laboratory instrument which required resolution is less than 1 mm in the vertical direction.

SUMMARY OF THE INVENTION

The present invention relates to a high resolution laboratory device which can determine salt concentration in water. A probe of electrical insulating material is provided with inner and outer electrodes. The inner electrode is positioned in a cavity and fluid enters this cavity by means of a horizontal slit and a small vertical hole. A sinusoidal current excitation source is connected to the electrodes and the electrical current density between the two electrodes is small except in the vertical hole where the current density becomes very large. The resistance between the electrodes at any instant is governed by the resistance of the fluid in the vertical hole and the resistance of the fluid is measured by determining the peak amplitude of the voltage drop across the vertical hole.

It is therefore a general object of the present invention to provide a high resolution instrument for measuring salinity in fluid.

Other objects, advantages and novel features of the invention will become apparent from the following detailed description of the invention when considered in conjunction with the accompanying drawing.

DESCRIPTION OF THE PREFERRED EMBODIMENT

Figure 1:
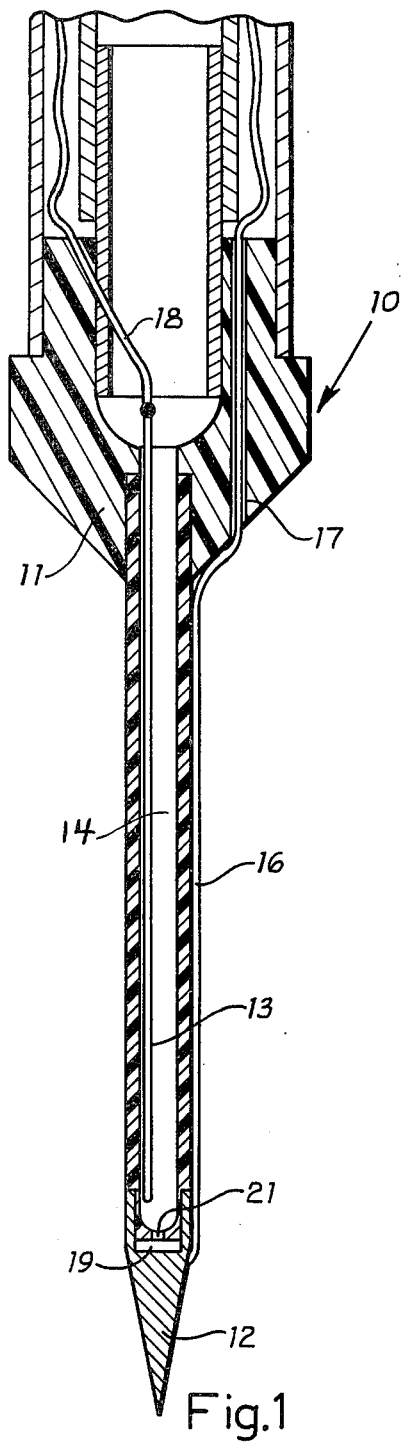
FIG. 1 is a sectional view showing a probe used in a preferred embodiment of the present invention.

Referring now to the drawings, there is shown in FIG. 1 a probe 10 of electrical insulating material 11, such as acrylic plastic. A first electrode 12, which is conical in shape, is attached to the electrical insulating material 11 and a second electrode 13 is positioned in a cavity 14 in the insulating material 11. A lead wire 16 is attached to electrode 12 and passes through a hole 17 in insulating material 11. Also a second lead wire 18 is attached to electrode 13.

Fluid enters into cavity 14 by means of a horizontal slit 19 between insulating material 11 and electrode 12, and a small diameter vertical hole 21 in insulating material 11. As shown in FIG. 1 of the drawings, slit 19 extends through the probe so that fluid can enter into cavity 14 from two sides. By way of example, a probe has been successfully used having a slit 19 which was 0.50 mm wide and the diameter of the vertical hole 21 was 0.30 mm.

Figure 3:
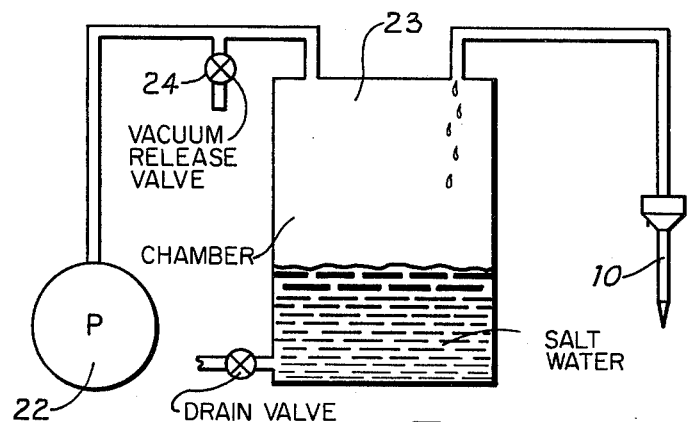
FIG. 3 is a diagrammatic view of a vacuum system for the probe shown in FIG. 1 of the drawings.

Referring now to FIG. 3 of the drawings, probe 10 is connected to a vacuum pump 22 by tubing and a cylindrical chamber 23. As the pressure drop in vertical hole 21 is large, pump 22 must be capable of developing low suction pressure and operating at a very low flow rate, and the pump 22 and cylindrical chamber 13 combination provide the desired function. A T-valve 24 is provided between pump 22 and chamber 23 to regulate the pressure in chamber 23 and therefore the flow rate through probe 10.

Excitation of probe 10 is provided by a sinusoidal current source 25. By way of example, sinusoidal current source 25 might be comprised of an impedance load connected to the output of a signal generator. Leads 16 and 18 connect probe 10 with sinusoidal current source 25. The resistance between electrodes 12 and 13 is utilized as a sensor element through which the excitation current flows and the voltage drop across it is coupled to a differential amplifier 27. The outputs from differential amplifier 27 are coupled to an output amplifier 28 through a simple rectifier and filter 29. Amplifier 28 is provided with an adjustable d.c. offset and gain to allow some choice of the output voltage range.

Figure 4:
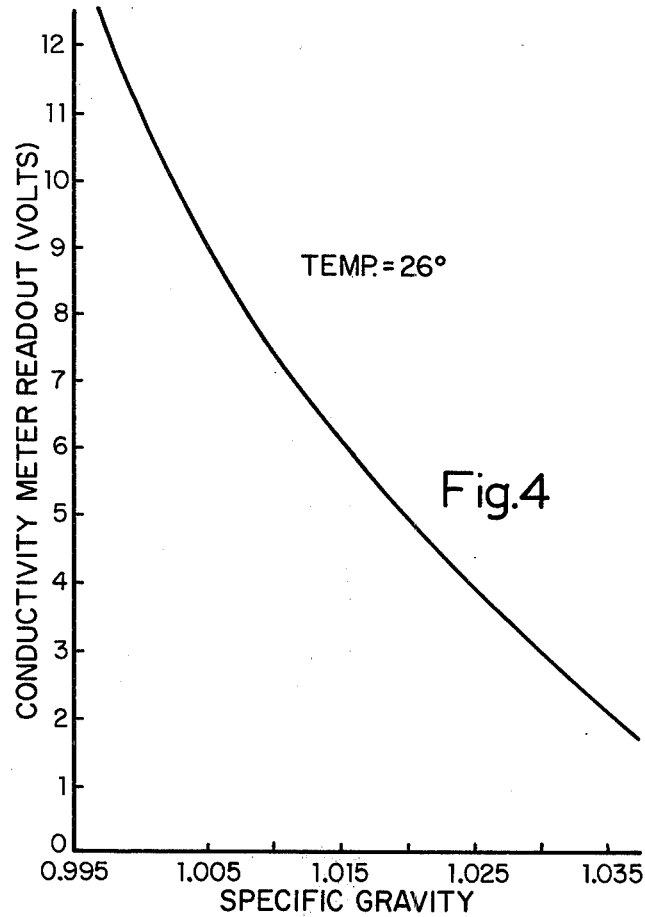
FIG. 4 is a calibration curve for the probe shown in FIG. 1 of the drawings.
Figure 2:
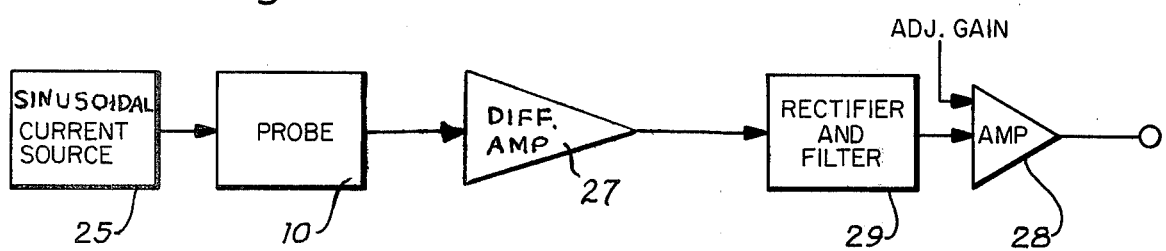
FIG. 2 is a block diagram of the conductivity probe electronics.

Referring to FIG. 4 of the drawings, there is shown a calibration curve for an instrument constructed according to the teachings of the present invention. A probe 10 was placed in a maximum NaCl solution of interest and the d.c. offset control of amplifier 28 was adjusted to obtain an output voltage of 0. Next, probe 10 was placed in a solution predetermined to be the minimum concentration of interest and the gain was adjusted to obtain an output voltage of 12 volts. Then solutions of intermediate NaCl concentrations were used to obtain points for the calibration curve shown in FIG. 3 of the drawings. As resistance changes with temperature change, the curve shown in FIG. 3 was made for a solution having a temperature of 26° C. Various other curves can readily be made for solutions at different temperatures. Temperature measurements are preferably made near the probe and at the elevation of slit 19.

OPERATION

In operation, probe 10 might be attached to a vertically movable device so that probe 10 might be lowered and raised in a tank of density stratified fluids which has been achieved by varying the concentration of salt. Such salt concentration gradients are found in nature, such as in the case of estuaries, mouths of rivers and the like. Pump 22 draws fluid through slit 19 and vertical hole 21 at a very low flow rate and the electrical current density between electrodes 12 and 13 is small except in vertical hole 21 where it becomes very large. The resistance between electrodes 12 and 13 at any instant is thus governed by the resistivity of the fluid in vertical hole 21. The resistance is measured using current excitation which produces a voltage drop that is processed to obtain an output voltage which can then be converted to specific gravity by using a chart such as is shown in FIG. 4 of the drawing.

It can thus be seen that the present invention provides a high resolution instrument for determining salt concentration in water by measuring the electrical conductivity of the salt water.

Obviously many modifications and variations of the present invention are possible in the light of the above teachings. It is therefore to be understood that within the scope of the appended claims the invention may be practiced otherwise than as specifically described. We claim:

1. An instrument for determining salt concentrations in fluid comprising,
    a probe having a chamber therein,
    a narrow vertical hole connected with said chamber and a narrow horizontal slit connected with said vertical hole for providing a passageway for admitting fluid into said chamber,
    first and second electrodes spaced apart from one another with said second electrode being attached within said chamber,
    means for continually drawing fluid through said slit and vertical hole into said chamber,
    means for applying a steady state alternating current between said first and second electrodes, and
    circuit means for measuring the resistance between said first and second electrodes and providing direct current output voltages inversely proportional to the amount of salt in said fluid.

2. An instrument for determining salt concentrations in fluid as set forth in claim 1 wherein said first electrode is conical and said horizontal slit extends through said second electrode from side to side.

3. An instrument for determining salt concentrations in fluid as set forth in claim 1 wherein said means for applying a steady state alternating current between said first and second electrodes includes a signal generator and a resistive load connected between said signal generator and said probe.

4. An instrument for determining salt concentrations in fluid as set forth in claim 1 wherein said means for continually drawing fluid through said slit and vertical hole into said cavity includes a vacuum pump connected to said cavity.

5. An instrument for determining salt concentrations in fluid as set forth in claim 4 wherein said pump is connected to said cavity in said probe through a auxiliary chamber whereby a low flow rate of fluid through said vertical hole is maintained.

* * * * *